United States Patent [19]

Bojar et al.

[11] Patent Number: 5,072,482

[45] Date of Patent: Dec. 17, 1991

[54] END BRUSH WITH MALE PROJECTION, APPARATUS AND METHOD FOR MAKING SAME, AND APPARATUS FOR USE THEREOF

[75] Inventors: James A. Bojar, Wauwatosa; Richard J. Shaw, Hartland, both of Wis.

[73] Assignee: Professional Dental Technologies, Inc., Batesville, Ark.

[21] Appl. No.: 402,341

[22] Filed: Aug. 31, 1989

[51] Int. Cl.$^5$ .................... A46B 1/00; A46D 1/04
[52] U.S. Cl. .................... 15/180; 300/21; 300/7
[58] Field of Search ............. 15/180, 28, 29, 167.1, 15/159 R, 160, 176.6, 179, 32, 39, 187; 300/21, 4, 7, 19; 433/125, 126, 128, 142, 147, 166

[56] References Cited

U.S. PATENT DOCUMENTS

| | | | |
|---|---|---|---|
| Re. 27,455 | 8/1972 | Lewis, Jr. | 300/21 |
| De. 295,801 | 5/1988 | Olsen | D4/101 |
| 1,259,571 | 3/1918 | Wiens | 300/21 |
| 1,280,944 | 10/1918 | Barry | 300/21 |
| 2,258,840 | 10/1941 | Beman | 15/187 |
| 2,531,481 | 11/1950 | Starr | 300/2 |
| 2,576,546 | 11/1951 | Starr | 300/21 |
| 2,664,316 | 12/1953 | Winslow, Jr. et al. | 300/21 |
| 2,672,640 | 3/1954 | Peterson et al. | 15/160 |
| 3,136,582 | 6/1964 | Locher et al. | 300/19 |
| 3,137,020 | 6/1964 | Tilgner | 15/179 |
| 3,186,018 | 6/1965 | Shaw | 15/159 A |
| 3,233,944 | 2/1966 | Shaw | 300/2 |
| 3,471,202 | 10/1969 | Lewis, Jr. | 300/2 |
| 3,596,999 | 8/1971 | Lewis, Jr. | 300/21 |
| 3,604,043 | 9/1971 | Lewis, Jr. | 15/59 |
| 3,633,974 | 1/1972 | Lewis, Jr. | 300/21 |
| 3,641,610 | 2/1972 | Lewis, Jr. | 15/114 X |
| 3,798,699 | 3/1974 | Lewis, Jr. | 300/21 |
| 3,799,616 | 3/1974 | Lewis, Jr. | 300/2 |
| 3,847,532 | 11/1974 | Bischoff | 425/500 |
| 3,910,637 | 10/1975 | Lewis, Jr. | 300/2 |
| 4,188,429 | 2/1980 | Braconnier et al. | 428/85 |
| 4,348,060 | 9/1982 | Lewis, Jr. | 300/21 |
| 4,365,313 | 1/1987 | Fassler et al. | 15/193 |
| 4,447,208 | 5/1984 | Kawai | 433/166 |
| 4,609,228 | 9/1986 | Bickel | 300/4 |
| 4,619,485 | 10/1986 | Lewis, Jr. | 300/21 |
| 4,690,277 | 9/1987 | Lewis, Jr. | 206/362.1 |
| 4,811,445 | 3/1989 | Lagieski et al. | 15/176.6 |
| 4,884,849 | 12/1989 | Shaw | 300/21 |

FOREIGN PATENT DOCUMENTS

| | | | |
|---|---|---|---|
| 1216014 | 12/1986 | Canada | 300/10 |
| 2561883 | 9/1984 | France | |
| WO84/00099 | 1/1984 | PCT Int'l Appl. | |
| 1221793 | 2/1971 | United Kingdom | |

*Primary Examiner*—Henry J. Recla
*Assistant Examiner*—David J. Walczak
*Attorney, Agent, or Firm*—William J. Sapone

[57] ABSTRACT

An end brush for use in a dental unit or the like includes a base formed of solified fiber material. The base includes an outwardly projecting portion, which is adapted to be received within a mounting structure provided on the dental unit. An apparatus and method for forming the end brush are disclosed.

4 Claims, 4 Drawing Sheets

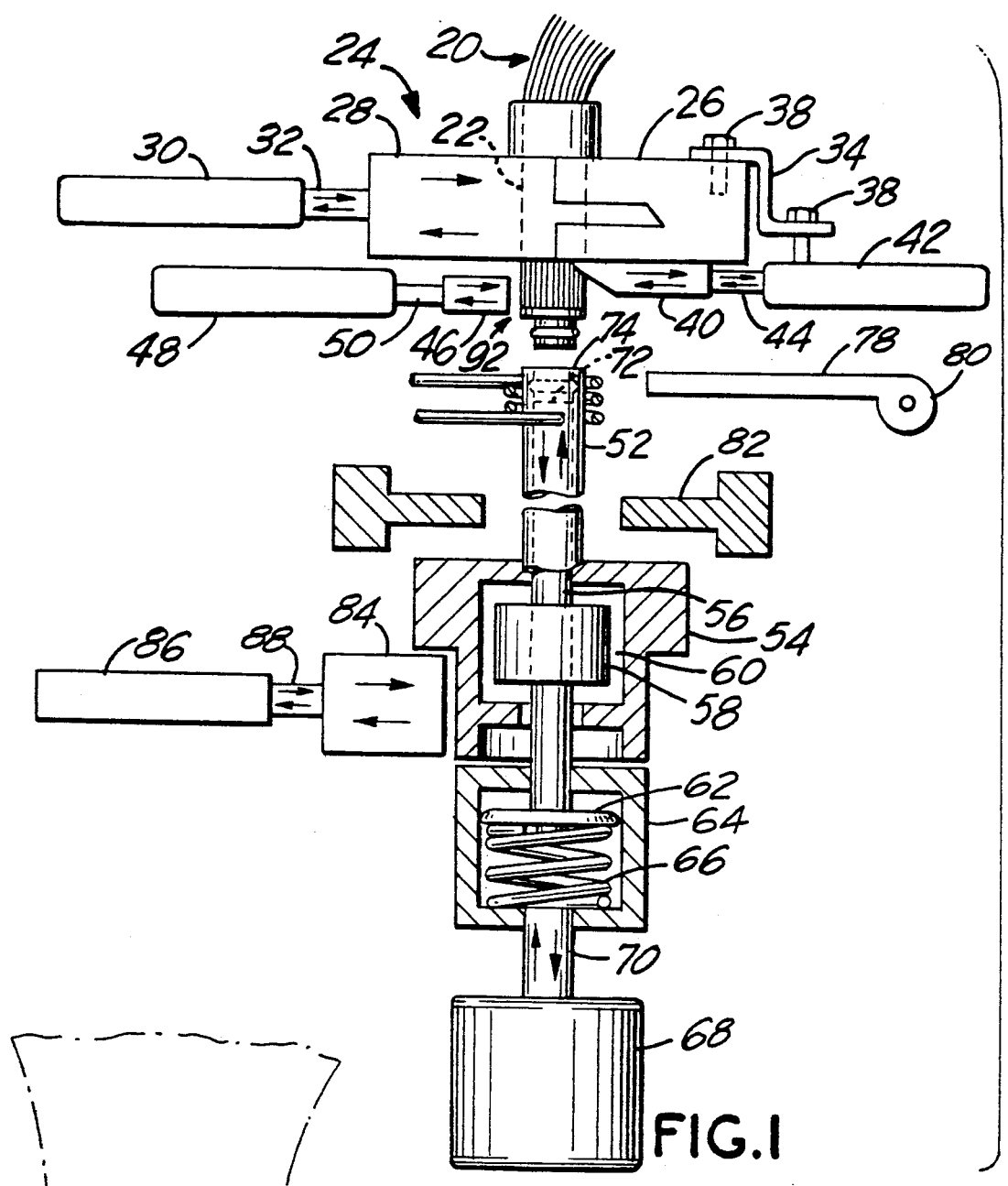
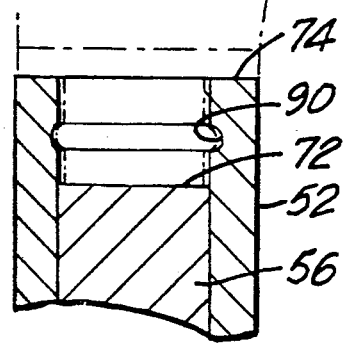
FIG.2
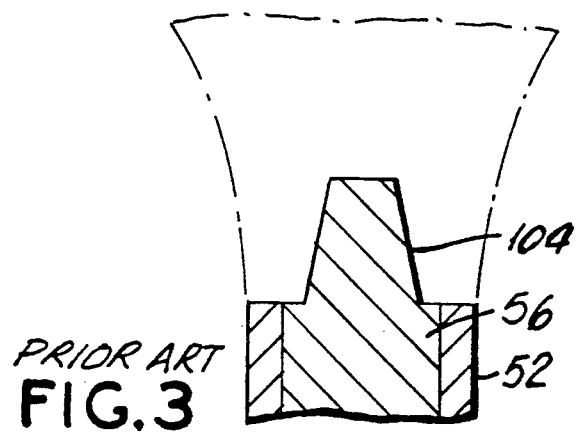
PRIOR ART
FIG.3

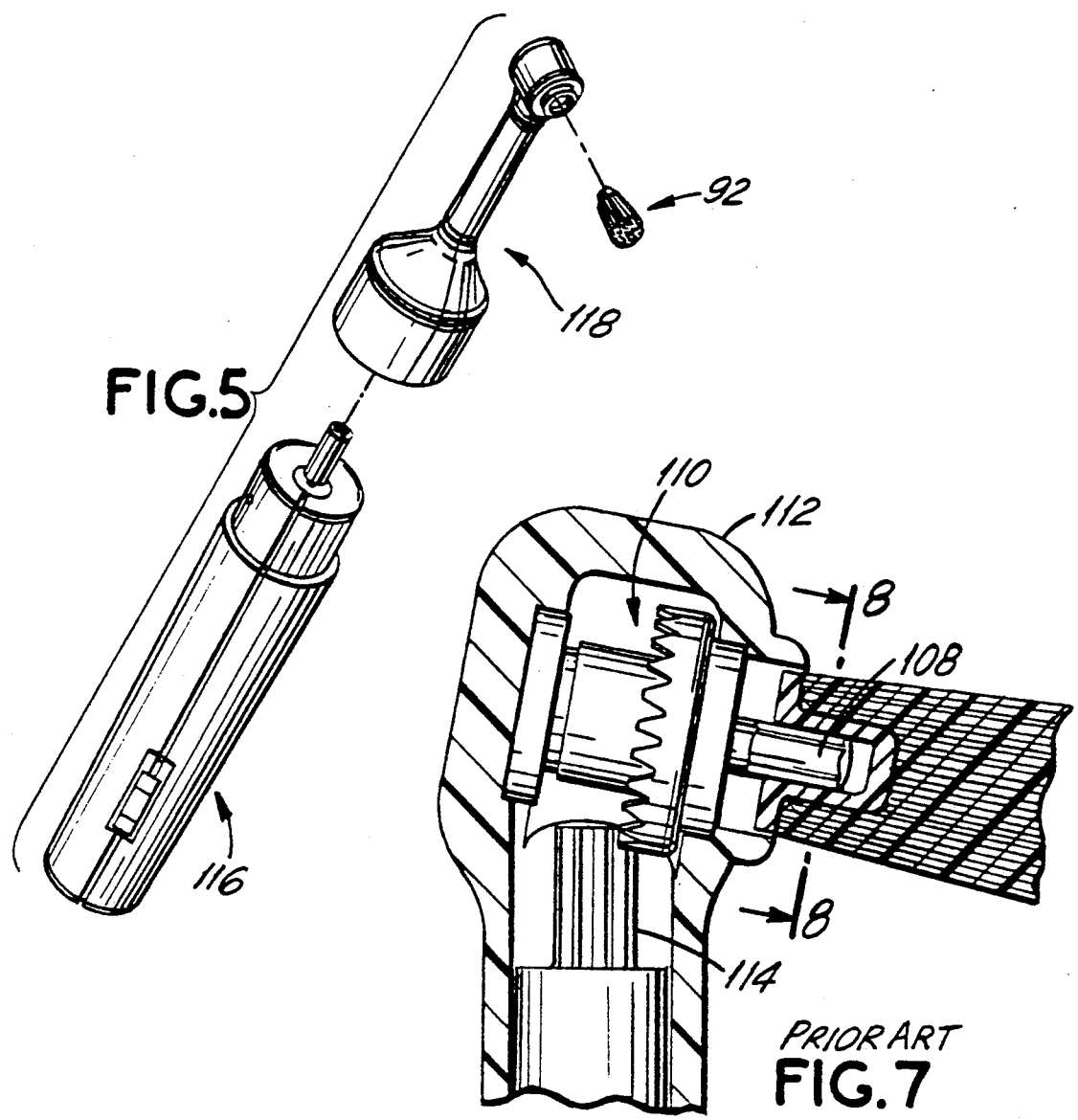
FIG. 5
FIG. 7 PRIOR ART
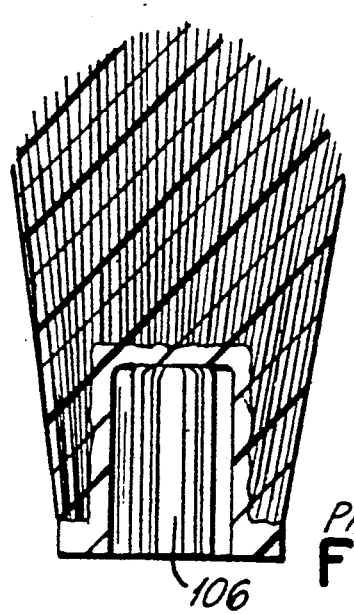
FIG. 6 PRIOR ART
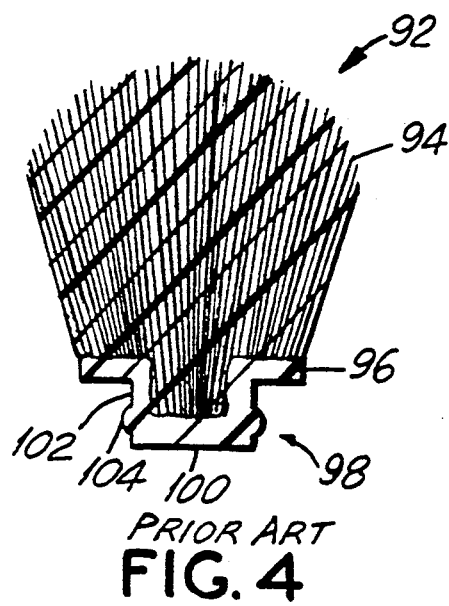
FIG. 4 PRIOR ART

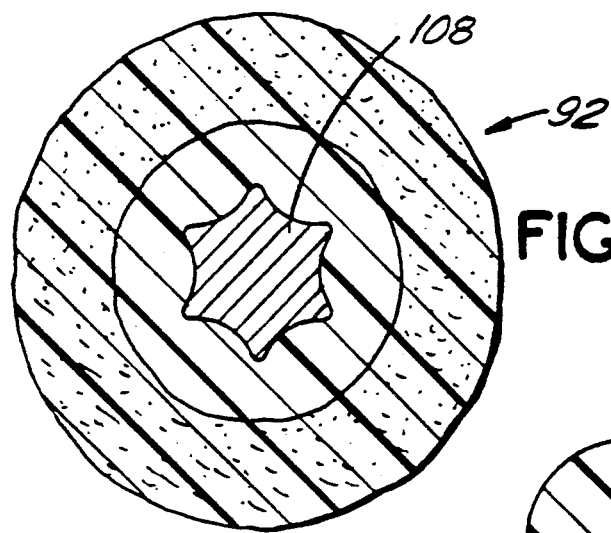
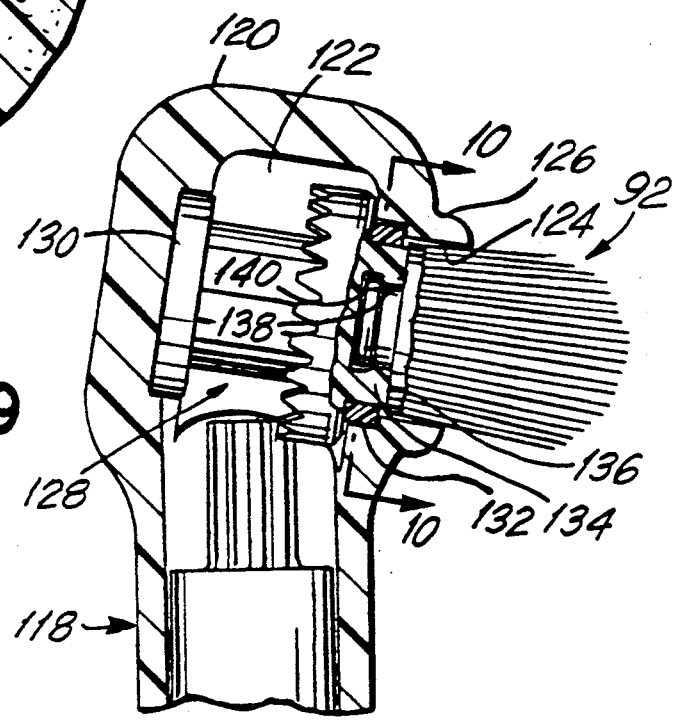
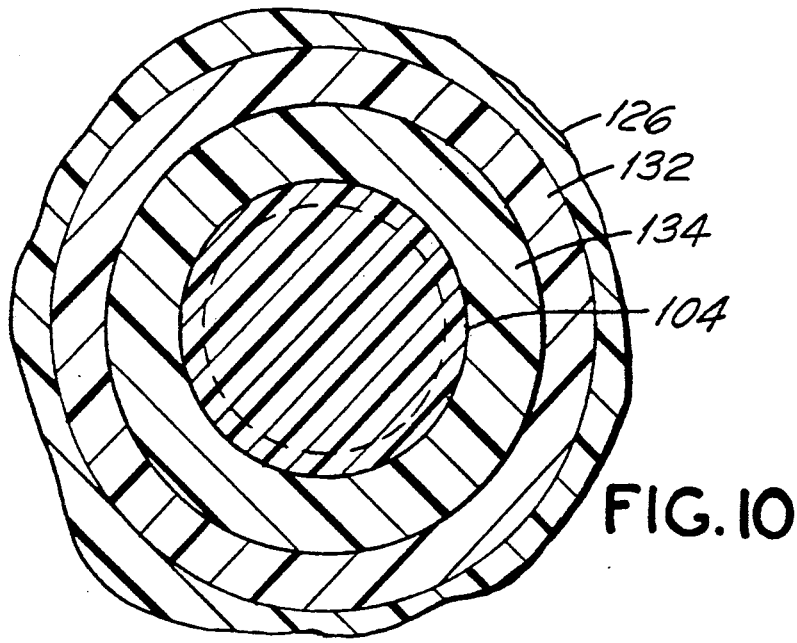

END BRUSH WITH MALE PROJECTION, APPARATUS AND METHOD FOR MAKING SAME, AND APPARATUS FOR USE THEREOF

BACKGROUND AND SUMMARY

This invention relates to an end brush formed of a bundle of thermoplastic fibers, in which one end of the bundle of fibers is formed of solidified fiber material. This type of brush is useful in an apparatus for cleaning the teeth, wherein rotation is imparted to the brush.

It is known to form an end brush from a bundle of thermoplastic fibers in which an end of the fiber bundle is subjected to a heating step so as to melt the fiber ends, and to thereafter cool the melted fiber material so as to provide a substantially rigid base to the end brush.

Application Ser. No. 07/283,089, filed Dec. 12, 1988 discloses an end brush of this type, and also an apparatus for manufacture thereof. In the noted application, the resultant end brush has a base formed of solidified fiber material, and a passage formed in the base. The passage has splined walls formed by insertion of a heated male splined pin into the fiber ends. The heated pin melts the fibers as it is inserted into the fiber bundle. After the heated pin is withdrawn from the fiber bundle and the melted fiber material has cooled, the melted fiber material forms a substantially rigid base for the end brush. The brush is then placed onto a dental unit which includes a rotating driveshaft having a splined configuration similar to that of the passage former in the base of the end brush, for imparting rotation thereto. An apparatus with which such a brush is useful is disclosed in U.S. Pat. No. 4,827,552 issued May 9, 1989.

While the end brush as described above has proven satisfactory in construction and operation, it has been found that cost savings and quality enhancements are attainable over the known brush and apparatus. The present invention is directed to this end.

In accordance with the invention, a brush assembly, such as for use in a dental unit, comprises a brush formed of a bundle of fibers extending from a base. The base is formed of solidified fiber material and includes an outwardly extending dimensionally defined projection. Drive means is provided for imparting rotation to the brush, and mounting means is associated with the drive means for securing the brush thereto. The mounting means includes a recess adapted to receive the outwardly extending projection of the base of the brush. Means is provided for securing the outwardly extending projection of the base of the brush within the recess. The projection is formed of solidifies fiber material, and preferably includes a transversely enlarged portion. The securing means comprises an area associated with the recess for receiving the transversely enlarged portion, so that the brush provides a snap-fit onto the mounting means by a push-on force mating the projection with the recess.

With this construction, the driveshaft in the known tooth cleaning apparatus can be eliminated, and is replaced by mating of the projection with the recess provided in the mounting means. The recess is preferably formed in an outwardly facing surface of a gear, which is adapted to be rotatably driven by the dental unit drive system, for imparting rotation to the brush. In a preferred embodiment, positive engagement means is provided for preventing slippage of the brush relative to the gear during operation. The positive engagement means may include a rib formed on the base of the brush protruding laterally from the projection and, means associated with a wall of the recess for engaging the protrusion so as to prevent slippage.

The invention also contemplates an end brush constructed substantially in accordance with the above description.

Also contemplated by the invention is a method of forming an end brush. The method includes providing a bundle of generally parallel fibers formed of thermoplastic material, and liquifying the fiber ends at an end of the bundle so as to unite the fibers. The liquified fiber material is formed to a shape providing an outer portion lying in a first plane substantially perpendicular to the fibers, and an inner portion extending below the outer portion so as to form a projection. The liquified fiber material is then solidified, so as to form a rigid base. In a preferred embodiment, the fiber ends are liquified by moving a heated element into engagement with the fiber ends so as to melt the fibers. Thereafter, the melted fiber material is cooled so as to solidify the material and form the base. The liquified fiber material is formed by providing the heated element with an upper outer surface and in inner surface disposed therebelow. Movement of the heated element into contact with the fiber ends melts the fiber material adjacent the fiber ends so that the melted fiber material conforms to the shape of the heated element. The melted fiber material adjacent the upper outer surface forms the outer portion, and the melted fiber material adjacent the inner surface forms the inner portion projecting below the outer portion. In a preferred embodiment, the heated element comprises an outer sleeve with a movable insert. Upward movement of the pin after the melted fiber material as solidified knocks the brush off of the heated element, preparing the heated element for subsequent usage in forming another brush.

The invention finally contemplates an apparatus for forming an end brush from a bundle of thermoplastic fibers. The apparatus comprises means for receiving the bundle of fibers and selectively clamping the bundle adjacent an end thereof. A movable element is movable into contact with the end of the fiber bundle. Heating means is provided for heating the movable element prior to contact with the fiber ends, so that the fiber ends are liquidified when the movable element is brought into contact therewith. The movable element is provided with means for forming the liquified fiber material to a shape providing an outer portion lying in a first plane substantially perpendicular to the fibers, and an inner portion extending below the outer portion so as to form a projection. The apparatus includes cooling means for solidifying the melted fiber material so as to form a rigid base. As described previously, the movable element preferably comprises a tubular sleeve, with an insert or pin disposed within the sleeve. The upper end of the pin is disposed below the upper end of the sleeve when the movable element is moved into contact with the fiber ends. The forming means thus comprises the upper end of the sleeve providing the outer portion, and the cavity formed by upper end of the pin and the inner wall of the sleeve providing the inner portion. The inner wall of the sleeve is preferably provided with a circumferential groove or indentation disposed above the upper end of the pin. In this manner, when the movable element is brought into contact with the fiber ends, melted fiber material flows into the indentation to provide an area of enlarged transverse dimension to the projecting portion of the brush base.

BRIEF DESCRIPTION OF THE DRAWINGS

The drawings illustrate the best mode presently contemplated of carrying out the invention.

In the drawings:

FIG. 1 is an elevation view of an apparatus for manufacturing an end brush according to the invention;

FIG. 2 is an enlarged partial elevation view, in section, showing the components of the apparatus of FIG. 1 for forming the male projection on the base portion of the end brush;

FIG. 3 is a view similar to FIG. 2, showing a prior art apparatus for forming an end brush in which a substantially central passage is provided in the base of the brush;

FIG. 4 is a cross sectional view of an end brush as manufactured according to the invention;

FIG. 5 is a view of a prior art removable head tooth cleaning apparatus with which an end brush made according to the invention is useable:

FIG. 6 is a cross sectional view similar to FIG. 4, showing a brush made according to the prior art apparatus as shown in FIG. 3;

FIG. 7 is a view of the prior art brush of FIG. 6 as installed on a dental unit, which includes a driveshaft for mating with the passage formed in the base of the end brush:

FIG. 8 is a sectional view taken generally along line 8—8 of FIG. 7;

FIG. 9 is a view similar to FIG. 7, showing an end brush according to the invention as installed on a dental unit, including means for receiving the male projection formed on the base of the end brush;

FIG. 10 is a partial sectional view taken generally along line 10—10 of FIG. 9;

DETAILED DESCRIPTION

Figure 11:
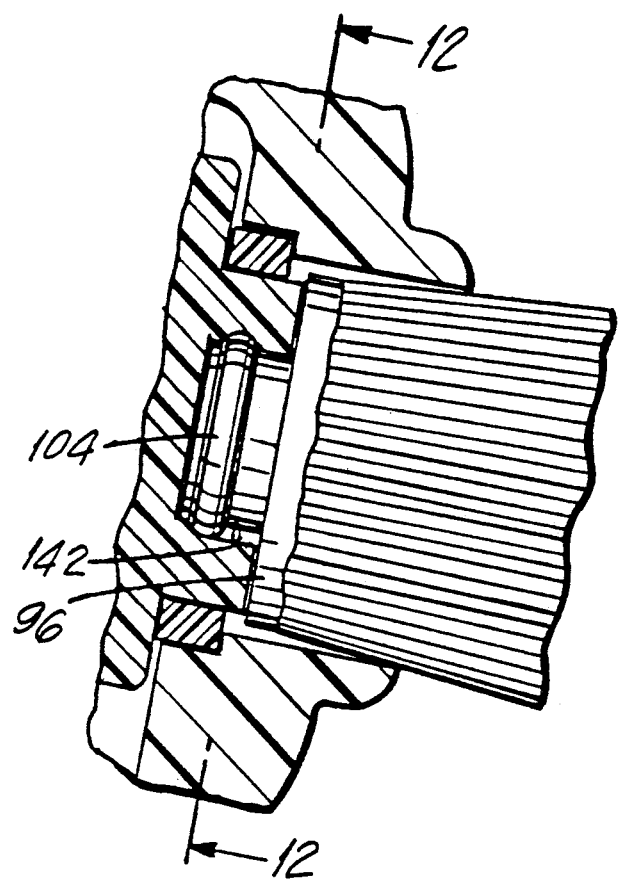
FIG. 11 is an enlarged partial elevation view of a portion of FIG. 9, showing a positive engagement system between the base portion of the end brush and the gear in which it is mounted.

With reference to FIG. 1, an apparatus for manufacturing an end brush is disclosed, substantially similar in construction to that as disclosed in application Ser. No. 07/283,089 filed Dec. 12, 1988, now U.S. Pat. No. 4,884,849, the disclosure of which is hereby incorporated by reference. While the apparatus of FIG. 1 is well described in the noted patent, a brief description of the apparatus will be undertaken.

A fiber bundle 20 is fed through an adjustable aperture 22 formed in an aperture plate 24. Aperture plate 24 consists of a stationary end 26 and a movable end 28, with a fluid-operated cylinder 30 interconnected with movable end 28 via a connecting rod 32. Stationary end 26 is held in place by means of a z-bracket 34 and bolts 36, 38. Pressurized fluid is selectively supplied to either the rod end or the piston end of cylinder 30, for selectively moving movable end 28 leftward or rightward, as desired. Upon full rightward movement of movable end 28, fiber bundle 20 is clamped within aperture 22 between movable end 28 and stationary end 26. When movable end 28 is moved leftwardly, the clamping force on bundle 20 is released, thereby allowing bundle 20 to be moved through aperture 22.

A reciprocable cutoff knife 40 is located below aperature plate 24. Knife 40 is interconnected with a fluid operated cylinder 42 via a connecting rod 44. Knife 40 is movable leftwardly and rightwardly upon the selective supply of fluid pressure to either the rod end or the piston end of cylinder 42.

A knock-off hammer 46 is located slightly below cutoff knife 40, and is interconnected with a fluid operated cylinder 48 via a connecting rod 50. Upon selective supply of fluid pressure to either the rod end or the piston end of cylinder 48, hammer 34 is reciprocably movable in a back and forth direction.

In accordance with the present invention, an outer sleeve 52 is connected at its lower end to a stop collar 54. An insert, or pin, 56 extends through the passage of sleeve 52. A collar 58 is formed on pin 56, and is disposed within a cavity 60 formed in stop collar 54. The lower end of pin 56 is provided with a flanged base 62, located within a housing 64. A spring 66 is provided between base 62 and the lower surface of housing 64, for biasing pin 56 upwardly. Housing 64 is interconnected with a fluid operated cylinder 68 via a connecting rod 70. Upon selective provision of pressurized fluid to either the rod end or the piston end of cylinder 68, housing 64 is reciprocably movable in an up-down direction.

The upper end of pin 56, shown at 72, is normally disposed below the upper end of sleeve 52, shown at 74. As will be explained, pin 56 is movable relative to sleeve 52 during operation.

An induction heating coil 76 circumferentially surrounds the upper portion of pin 56.

At approximately the same elevation as heating coil 76, a cold air nozzle 78 interconnected with a cold air supply 80 is provided.

Upper stationary stops 82 are positioned above stop collar 54. A lower stop plate 84 is positioned below stop collar 54, and is interconnected with a fluid operated cylinder 86 via a connecting rod 88. Upon selective provision of fluid pressure to either the rod end or the piston end of cylinder 86, lower stop 84 is reciprocably movable in a back and forth direction.

Referring to FIG. 2, the relationship of sleeve upper end 74 and pin upper surface 72 is illustrated. As shown, a circumferential groove 90 is formed in the inner wall of sleeve 52. Groove 90 is located above pin upper surface 72, and is spaced below sleeve upper end 74.

In operation, the above-described apparatus functions as follows. Movable end 28 of aperture plate 24 is moved leftwardly so as to open aperture 22. The leading end of fiber bundle 20 is fed through aperature 22 until it is flush with the bottom surface of aperature plate 24. Movable end 28 of aperture plate 24 is then moved rightward to its closed position, so as to clamp fiber bundle 20 into aperture 22. Induction heating coil 76 is then actuated, so as to heat the upper portion of sleeve 52, as well as the upper end of pin 56. Fluid pressure is then supplied to the piston side of cylinder 68, so as to extend rod 70 and move housing 64 and collar 54 upwardly until the upper surface of collar 54 contacts the lower surface of upper stops 82. This action forces upper end 74 of sleeve 52 into the fiber ends, which are melted due to the high temperature of sleeve 52 produced by heating of induction coil 76. The liquified fiber material conforms to the configuration of the upper portion of sleeve 52, as shown in FIG. 2, and flows downwardly into the passage in sleeve 52 into contact with upper end 72 of pin 56. The melted fiber material flows into circumferential groove 90. After full upward movement of the sleeve and pin assembly, and sufficient time has passed so as to allow the melted fiber material to conform to the configuration of the upper end of the sleeve and pin assembly, a cold air blast from cold air nozzle 78 is then directed onto the upper portion of sleeve 52. This acts to cool sleeve 52 and thereby solidify the melted fiber material. Movable end 28 of aperture plate 24 is then opened, and fluid pressure supplied to the rod side of cylinder 68 so as to move the sleeve and pin assembly downwardly, thus drawing fiber bundle 20 through aperture 22 in aperture plate 24. After fiber bundle 20 is drawn down a predetermined distance, fluid pressure is supplied to cylinder 42 so as to actuate cutoff knife 44, severing fiber bundle 20 a predetermined distance above the fused fiber ends. The sleeve and pin assembly is then drawn down further while stop collar 54 is held stationary by lower stop 84, so as to move, and pin 56 upwardly within sleeve 52 to eject the formed brush from the upper end of sleeve 52. Knock off hammer 46 is then actuated for removing the formed brush from the apparatus, whereafter sleeve 52 is then moved upwardly in preparation for another cycle.

While the above-described apparatus and method have been formed satisfactorily, it is contemplated that various changes may be made in order to effect a more efficient, higher-production operation.

With reference to FIG. 4, a brush 92 made according to the above-described and apparatus and process is illustrated. Brush 92 includes a plurality of fibers 94 extending outwardly from a base formed of solidified fiber material. Fibers 94 are preferably such as sold by E. I. duPond deNemours under its trademark "Tyvex". As shown, the base includes an outer portion 96 lying in a plane substantially perpendicular to fibers 94. A substantially cylindrical inner portion 98 extends below outer portion 96. Inner portion 98 results from the melted bristle material conforming to the configuration of the upper end of the sleeve and pin assembly as shown in FIG. 2. Inner portion 98 includes a substantially flat end portion 100 and a sidewall portion 102. A lateral protrusion 104 is provided on sidewall portion 102, resulting from melted bristle material flowing into circumferential groove 90 formed in the inner wall of sleeve 52. Protrusion 104 is located toward the lower end of sidewall 102.

As is seen, outwardly extending fibers 94 are integrally attached at their lower ends to the solidified base, due to the melting of fiber material which forms the base. The fibers extend through the interior of cylindrical inner portion 98, for connection to cylindrical portion end wall 100.

Referring to FIG. 3, the prior sleeve and pin assembly for forming the end brush is illustrated. Like reference characters will be used to facilitate clarity. A splined projection 104 is formed at the upper end of pin 56. The sleeve and pin assembly is maintained in its FIG. 3 position and moved upwardly into the end of the fiber bundle, after heating of the upper portion of the sleeve and pin assembly. Projection 104 is forced into the fibers, and the fiber ends are melted so as to form a base corresponding the shape of the upper end of the sleeve and pin assembly.

A brush made according to this method is shown in FIG. 6, and includes a splined axial passage 106 formed by splined projection 104 after withdrawal from the fiber bundle and cooling of the melted fiber material. As shown in FIG. 7, splined passage 106 is adapted to mate with a male splined driveshaft 108 projecting outwardly from a crown gear 110 rotatably mounted within the end portion 112 of a brush head. Upon rotation of crown gear 110 by means of rotation of a drive gear 114, rotation is imparted to drive shaft 108, and positive engagement of driveshaft 108 with the spline in the wall of passage 106 imparts rotation to the brush.

FIG. 8 illustrates the configuration of the splines on driveshaft 108, and on the walls of passage 106.

Referring to FIG. 5, end brush 92 constructed according to the convention is adapted for use in a tooth cleaning instrument comprising a hand-held power unit 116 and a removable head portion 118. Power unit 116 and head 118 are preferably such as manufactured by Better Health Concepts, Inc. of Wauwatosa, Wis. under its trademark "Proclean 2000". Referring to FIGS. 5 and 7, the drive configuration illustrated in FIG. 7 is a prior art drive system, and FIG. 5 is modified to accept brush 92 as manufactured in accordance with the present invention. Such a system is disclosed in FIG. 9, and reference is made thereto for a detailed explanation of the interrelationship of brush 92 with removable head 118.

Head 118 includes an end housing 120 provided with a hollow interior 122 opening outwardly through a passage 124 in part defined by a circumferential lip 126. A crown gear 128 is rotable mounted within hollow interior 122 of end housing 120. A rear thrust collar 130 is placed within a recessed area formed in end housing 120, and the rear end of crown gear 128 is received within rear thrust collar 130. A forward thrust collar 132 is placed in a forward recess formed in hollow interior 122, and receives the neck 134 of crown gear 128. Crown gear 128 includes an outwardly facing forward surface 136.

An outwardly facing recess is formed in forward surface 136 of crown gear 128, and is adapted to accept the cylindrical inner portion 98 of the base of brush 92. The recess formed in crown gear 128 includes an outer restricted portion 138 and an inner expanded portion 140.

Brush 92 is adapted to be snap-fit into the recess formed in forward surface 136 of crown gear 128. The snap-fit is accomplished by forcing circumferential protrusion 104 formed at the base of brush 92 through the recess restricted portion 138 until protrusion 104 snaps into recess expanded portion 140. The depth of recess restricted portion 138 is substantiably equal to, or slightly greater than, the portion of sidewall 102 in the base of brush 92 between the uppermost surface of protrusion 104 and the lowermost surface of outer base portion 96. In this manner, a secure engagement of protrusion 104 with the shoulder formed between recess expanded portion 140 and restricted portion 138 is ensured. The lower surface of base outer portion 96 contacts the area of crown gear forward surface 136 adjacent the recess formed therein.

The resiliency provided to the cylindrical projection 98 formed at the base of brush 92 accommodates repeated removal and reconnection of brush 92 to crown gear 128, as often as desired by the user.

Circumferential lip 126 provides lateral support for the outwardly extending fibers of brush 92, preventing flaring of the fiber material during use.

As can be seen, the provision of cylindrical projection 98 mating with the recess formed in crown gear outer surface 136 eliminates the need for driveshaft 108 to secure brush 92 to crown gear 128, as was required in the prior art embodiment shown in FIG. 7. This elimination of driveshaft 108 substantially reduces the cost of manufacture of removable head 118, both due to elimination of the component part as well as the labor involved in installing the part. In a typical package offered for sale, two of the removable heads such as 118 are provided to the customer. The construction as shown in FIG. 9 thus becomes even more cost reductive.

In addition, certain benefits are offered by the design of brush 92 over the prior art brush as shown in FIGS. 6 and 7. Referring to FIG. 4, it is seen that the overall height of brush 92 is less than the prior art brush. In the prior art brush, the central bristles, which perform the majority of the work on the tooth surfaces during operation, are of a length extending above the upper surface of the solidified end wall of passage 106. This length of such fibers is the critical length, in that a certain amount of stiffness is desired in order to adequately perform the work desired. If the length of the fibers above the upper end wall of passage 106 is too long, the fibers will be too floppy. On the other hand, if the length of the fibers is too short, the fibers will be too stiff and abrasive action on the teeth and gums will result. Accordingly, the length as shown in FIG. 6 is appropriate. The same length of the central fibers can be achieved with the design of brush 92 as shown in FIG. 4 with a substantial overall reduction in the length of the brush. This is because the length of the central fibers, due to the presence cylindrical projecting portion 98 on the base of brush 92, extends throughout substantially the entire height of the brush, and is not limited by the central passage as was the case with the prior art brush of FIG. 6. This reduction in the overall length of the brush is significant, in that a person's mouth presents only a certain amount of working room between the outer tooth surfaces and the inner surface of the cheek. This is especially significant in the case of younger users, whose mouths are necessarily smaller and contain even less clearance room than does an adult's mouth, without compromising the degree of stiffness of the brush.

Figure 12:
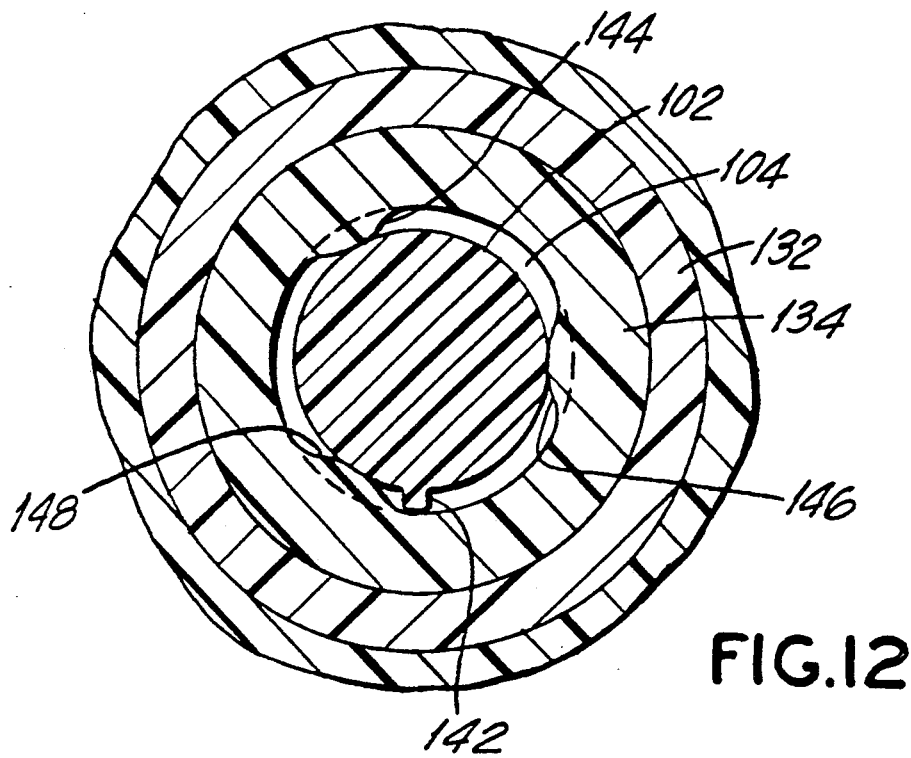
FIG. 12 is a partial sectional view taken generally along line 12—12 of FIG. 11.

With reference to FIGS. 11 and 12, a positive engagement system is preferably provided between cylindrical projecting portion 98 of the base of brush 92 and the portion of crown gear 128 forming the recess within which projecting portion 128 is received. As shown in FIG. 11, an integrally molded rib 142 extends between protrusion 104 and the lower surface of base outer portion 96. Rib 142 is simultaneously formed with the base of brush 92 of solified bristle material, by slightly modifying the sleeve and pin assembly of FIG. 2.

Referring to FIG. 12, crown gear 128 is modified so as to provide spaced inwardly extending lobes 144, 146 and 148. Lobes 144-148 form restricted portion 138 of the recess in crown gear outer surface 136, so as to provide a 3-point contact with the outer surface of sidewall 102 of cylindrical projection 98. Protrusion 104 formed on cylindrical projecting portion 98 is again adapted for a snap-fit into expanded portion 140 of the recess in crown gear 128, past lobes 144-148. Upon rotation of crown gear 128 during operation, rib 142 is moved into contact with one of lobes 144-148, which contact thereafter prevents further rotation of brush 92 due to engagement of rib 142 with the lobe. In this manner, slippage between brush 92 and crown gear 128 is prevented.

Various alternatives and embodiments are contemplated as being within the scope of the following claims particularly pointing out and distinctly claiming the subject matter regarded a the invention.

I claim:

1. An end brush comprising:
a plurality of generally parallel fibers bundle to form a brush having first and second ends; and, a base formed at said first bundle end by solidifying said fibers, said fibers extending away from said base and terminating in said second end, the base having a first portion disposed in a plane substantially perpendicular to the fibers and a projecting portion extending from said first position in a direction opposite to said fibers, said projecting portion being of smaller diameter than said first portion, and having means for connecting the base to a means for rotating the brush, the projecting portion having a protrusion extending perpendicular to the projecting portion, for connecting the base to a means for rotating the brush, the protrusion spaced away from and substantially parallel to the first portion of the base.

2. The end brush of claim 1 wherein the projecting portion is substantiality cylindrical, the projecting portion having a side wall and an end wall formed of solidified fiber material, the fibers extending upwardly from the end wall of said projecting portion and being partially contained within the side wall of the substantially cylindrical projection.

3. An end brush comprising: a plurality of generally parallel fibers bundle to form a brush having first and second ends; and, a base formed of solidified fiber material, said fibers at said first bundle end by solidifying said fibers extending away from said base and terminating in said second end, the base having a first portion disposed in a plane substantially perpendicular to the fibers and a projecting portion extending from said portion in a direction opposite to said fibers, said projecting portion being of smaller diameter than said first portion, and having means for connecting the base to a means for rotating the brush, the connecting means being a rib extending outwardly from the projecting portion, between the projecting portion and a lower surface of the first portion.

4. The end brush of claim 3 wherein the projecting portion is substantially cylindrical, the projection portion having a side wall and an end wall formed of solidified fiber material, the fibers extending upwardly from the end wall of said projecting portion and being partially contained within the side wall of the substantially cylindrical projection.

* * * * *